United States Patent [19]
Botknecht et al.

[11] Patent Number: 5,885,597
[45] Date of Patent: Mar. 23, 1999

[54] TOPICAL COMPOSITION FOR THE RELIEF OF PAIN

[75] Inventors: Jonah Botknecht; Robert Fishman, both of Davie, Fla.

[73] Assignee: Medical Research Industries,Inc., Davie, Fla.

[21] Appl. No.: 942,184

[22] Filed: Oct. 1, 1997

[51] Int. Cl.$^6$ .......................................................... A61K 6/00
[52] U.S. Cl. .......................... 424/401; 514/946; 514/947; 514/944; 514/887; 514/886; 514/825; 514/817
[58] Field of Search .............................. 424/401; 514/817, 514/825, 886, 887, 944, 946, 947

[56] References Cited

U.S. PATENT DOCUMENTS

| | | |
|---|---|---|
| 4,340,594 | 7/1982 | Mizushima . |
| 4,465,663 | 8/1984 | Schmolka . |
| 4,783,450 | 11/1988 | Fawzi . |
| 4,997,853 | 3/1991 | Bernstein . |
| 5,141,738 | 8/1992 | Rasor . |
| 5,178,879 | 1/1993 | Adekunle et al. . |
| 5,318,960 | 6/1994 | Toppo . |
| 5,332,576 | 7/1994 | Mantelle . |
| 5,560,910 | 10/1996 | Crandall . |
| 5,639,740 | 6/1997 | Crandall . |
| 5,654,337 | 8/1997 | Roentsch et al. . |
| 5,665,378 | 9/1997 | Davis et al. . |

FOREIGN PATENT DOCUMENTS 405105628  4/1993  Japan .

OTHER PUBLICATIONS

The Merck Manual, 1992, 16th Edition, pp. 1297–1300.

*Primary Examiner*—Thurman K. Page
*Assistant Examiner*—Brian K. Seidleck
*Attorney, Agent, or Firm*—Robert M. Schwartz; Otto S. Kauder

[57] ABSTRACT

Disclosed is a topical composition for relieving pain in a person in need of such relief, consisting essentially of an effective amount of a combination of at least one corticoid analgesic, at least one arylpropionic acid type analgesic, and at least one p-aminobenzoic acid ester type local anesthetic; an amount effective in enhancing the effectiveness in relieving pain of the combination of capsaicin, and an amount effective to increase the transmission thereof of through the skin of at least one phospholipid and at least one polyoxyethylenepolyoxypropylene copolymer.

17 Claims, No Drawings

TOPICAL COMPOSITION FOR THE RELIEF OF PAIN

BACKGROUND OF THE INVENTION

1. Field of the Invention

This invention relates to the relief of pain, in particular to the control of pain by the topical application of a composition comprising a combination of remedies and certain adjuvants to enhance their effectiveness and assist transport of such remedies through a person's skin.

2. Prior Art

According to one of its aspects, this invention relates to the relief of pain. More particularly, this invention relates to the relief of pain generally deemed (by others than the sufferer) mild to moderate, such as headache, muscle ache, menstrual cramps, low back pain, arthralgia and the like for relief of which the so-called minor analgesics such as aspirin, acetaminophen, and ibuprofen are conventionally recommended. These minor analgesics are believed to have helped many people and are consumed in large quantities worldwide. They are, however, not free of unpleasant and even dangerous side effects, and new and improved remedies are constantly being sought.

This invention also relates to the relief of acknowledged severe pain for which controlled substance analgesics or narcotics are commonly offered. The concomitant dangers and drawbacks are well known and need no elaboration.

According to a further aspect, this invention relates to the relief of pain in one or more of a person's joints. More particularly, this invention relates to the relief of pain associated with those musculosketal disorders that primarily affect the joints. Joint disorders are further classified into the periarticular tissue disorders (eg tennis elbow) and the true articular or joint diseases (eg osteoarthritis). The MERCK MANUAL, 16th edition, published 1992, at pages 1297 to 1300, which portion is here incorporated by reference, contains a table titled "Classification of the Rheumatic Diseases" that includes ten major categories of disease including among others Diffuse Connective Tissue Diseases embracing rheumatoid arthritis and 17 other diseases and conditions; Arthritis associated with Spondylitis embracing 5 diseases and conditions; two kinds of Osteoarthritis; and 13 kinds of Arthritis, Tenosynovitis, and Bursitis associated with infectious agents. Most of these diseases and conditions are accompanied by pain. As pointed out by this publication, "we do not yet fully understand the causes of nor can we completely control joint pain."

Also according to this reference, a few types of arthritis are treatable with specific therapy; for example, gout can be completely controlled with drugs, or Lyme disease can be treated with antibiotics, but there are no "magic bullets" for most chronic rheumatic disorders. Optimal management for patients with severe musculosketeal disease requires many skills and resources and the collaboration of rheumatologists, orthopedic surgeons, paramedical specialists, and support services. Drug therapy is synergistic to other treatment in providing symptomatic control and suppression of disease and rarely should be relied alone. Disease suppression can be achieved with hypouricemic drugs for gout, corticosteroids and immunosuppressive agents for immunologic and inflammatory diseases, and a range of miscellaneous slow-acting drugs for rheumatoid arthritis and the arthropathies associated with spondylitis. Aspirin has been used for pain and inflammation since early in this century. More recent drug therapy for rheumatoid arthritis includes gold injections, penicillamine, hydroxychloroquine, and sulfasalazine. However, drug control of these conditions remains imperfect, and better understanding and new approaches are urgently needed.

For rheumatoid arthritis in particular, the same reference notes that among nonsteroidal anti-inflammatory drugs (NSAIDs), salicylates are relatively safe, inexpensive, analgesic, and anti-inflammatory, and are the traditional cornerstone of drug therapy in rheumatoid arthritis. Aspirin is begun with 600 to 1000 milligrams four times daily and adjusted upward until achieving a maximally effective or mildly toxic dose (eg tinnitus, diminished hearing) to a final dose from 3000 to 6500 milligrams per day. Other NSAIDs are available for patients who do not tolerate suficient aspirin to obtain a good effect, as shown in the following table:

| Agent | Recommended dosage |
|---|---|
| Indomethacin | 25 milligrms three or four times daily |
| Ibuprofen | 400–800 mg four times daily |
| Naproxen | 250 mg twice daily or up to 1250 mg/day |
| Fenoprofen | 300–600 mg four times daily, 3200 mg maximum |
| Tolmetin | 400 mg three times daily, 2000 mg maximum |
| Sulindac | 150–200 mg twice daily |
| Meclofenamate | 200–400 mg/day |
| Ketoprofen | 150–300 mg/day |
| Proxicam | 20 mg once daily |
| Flurbiprofen | 100 mg twice or three times daily |
| Diclofenac | 75 mg twice daily or 50 mg four times daily |

While less irritating to the gastrointestinal tract than aspirin, these NSAIDs can also produce gastric symptoms and bleeding.

Gold and the other slowly acting drugs are considered for use when aspirin or other NSAIDs are not sufficiently beneficial after 3 to 4 months of treatment. These drugs, too, are unfortunately subject to toxic side effects.

Corticosteroids are the most dramatically effective short-term anti-inflammatory drugs, but rheumatoid arthritis is usually active for years, and clinical benefit from corticosteroids often diminishes with time.

Thus, there clearly exists a need for ways to control pain that are both more safe and more effective.

Mizushima et al U.S. Pat. No. 4,340,594 discloses a fat emulsion for parenteral or oral administration, having anti-inflammatory activity, comprising an anti-inflammatory steroid, soybean oil, a phospholipid, and water. The fat emulsion is useful in the therapeutic or prophylactic treatment of rheumatism, immulogical hemolytic anemia, idiopathic thrombacytopenic purpura and Paget disease, or in conjunction with kidney transplantation. The fat emulsion may be compounded, as stabilizer, with a high molelcular substance selected from albumin, dextran, vinyl polymers, nonionic surface active agents, gelatin, and hydroxyethyl-starch. Polyoxyethylenepolyoxypropylene copolymer having average molecular weight 1000 to 20000 is disclosed as one kind of nonionic surfactant. There is no disclosure of any topical composition or administration of any agent through the skin.

Fawzi et al U.S. Pat. No. 4,783,450 discloses that lecithin enhances the penetration of a drug through the skin as well as a pharmaceutical composition adapted for transdermal administration comprising an active ingredient and an effective amount of lecithin. An active ingredient is defined as "an effective amount of any therapeutically active drug". The "preferred drugs" recited by categories and specific compounds include analgesics without any details.

Rasor et al U.S. Pat. No. 5,141,738 discloses an injectable contrast medium for use as an ultrasonic diagnostic agent, particularly for imaging the left side of the heart, comprising a liquid vehicle containing suspended therein (a) microparticles comprising a mixture of (i) a lipophilic surfactant and (ii) a non-surfactant water soluble solid inorganic salt, organic salt, or solid hydroxy compound, and (b) microbubbles to render the mediim ultrasonic image enhancing. A homeopathic trituration of galactose and magnesium stearate is disclosed as one such inorganic solid. However, conventional surfactants which have an HLB value above about 20, e.g. sodium lauryl sulfate, sodium dodecylbenzenesulfonate and the commercially available nonionic surfactants, e.g. the Pluronics, do not enhance practical left heart contrast; their use in conjunction with ultrasonic contrast agents intended for left heart imaging would appear to be contraindicated. There is no mention of transdermal administration of anything.

Mantelle U.S. Pat. No. 5,332,576 discloses a composition for topical application substantially free of water and substantially water insoluble comprising (a) a therapeutically effective amount of at least one local anesthetic, (b) a pharmaceutically acceptable solvent, and (c) a flexible, finite, polysaccharide bioadhesive carrier. The solvent is preferably a polyhydric alcohol or combination of polyhydric alcohols, ie any organic polyalcohol including dipropylene glycol, propylene glycol, polyethylene glycol, glycerin, butylene glycol, hexylene glycol, polyoxyethylene, polypropylene glycol, sorbitol, ethylene glycol, and the like. Lecithin can be included as a binder. Pharmaceutically active agents in the composition can include any of 48 categories and the individual members thereof disclosed at column 18 line 37 to column 21 line 23.

Crandall U.S. Pat. No. 5,639,740 discloses methods and compositions for topically treating keratinous structures of humans and animals including skin, hair, fingernails, toenails, hooves, and horns by topically applying a composition comprising lecithin, isopropyl palmitate and water, which composition is called lecithin organogel. Lecithin organogel is optionally included in combination with an approximately 20% solution of PLURONIC F-127 (BASF, Parsippany N.J.) otherwise known as poloxamer 407 in a ratio of approximately 1:4. Crandall's composition can include pharmaceutically acceptable components such as gelling agents, compounding agents, and scents, and other pharmaceutically active agents such as antibacterial, antifungal, antiprotozoal or antiviral agents. There is, however, no mention of any analgesic or anesthetic remedy or of treating pain or any condition not relating to keratinous structures.

SUMMARY OF THE INVENTION

In accordance with this invention, there is provided a topical composition for relieving pain in a person in need of such relief, consisting essentially of an effective amount of a combination of at least one corticoid analgesic, at least one arylpropionic acid type analgesic, and at least one p-aminobenzoic acid ester type local anesthetic; an amount effective in enhancing the effectiveness in relieving pain of the combination of capsaicin, and an amount effective to increase the transmission thereof of through the skin of at least one phospholipid and at least one polyoxyethylenepolyoxypropylene copolymer.

As a result of the advantageous interaction of the analgesic and local anesthetic substances and capsaicin in combination in this composition together with the increased transmission thereof through the skin, greatly effective relief of pain can be achieved with very modest dose levels of the active substances, unexpectedly greater than by administration of individual ingredients of the composition or of the whole composition by the oral route. There is further provided a method of relieving pain of a person in need of such relief by topically administering to said person a composition, consisting essentially of an effective amount of a combination of at least one corticoid analgesic, at least one arylpropionic acid type analgesic, and at least one p-aminobenzoic acid ester type local anesthetic; an amount effective in enhancing the effectiveness in relieving pain of the combination of capsaicin, and an amount effective to increase the transmission thereof of through the skin of at least one phospholipid and at least one polyoxyethylenepolyoxypropylene copolymer.

DESCRIPTION OF PREFERRED EMBODIMENTS

Relief of a person's pain by topical administration to such person of a topical composition of this invention can include the management and relief of pain in various parts of the body distant from the area to which the composition is applied, such as headache, muscle ache, menstrual cramps, low back pain, arthralgia and the like. It can also assist the relief of pain in a person's joints.

Phospholipids that can be used in the composition of this invention include phosphatidylcholine, phosphatidylethanolamine, and phosphatidylserine and mixtures thereof. The fatty acid groups in the phosphatidyl moieties of these phospholipids can be saturated, monounsaturated or polyunsaturated groups such as lauroyl, linoleyl, myristoyl, oleoyl, palmitoyl, and stearoyl groups. Soy lecithin, a mixture of phospholipids rich in monounsaturated and polyunsaturated phosphatidylcholines is particularly preferred.

Any polyoxyethylenepolyoxypropylene copolymer can be used in the composition of this invention. Thus the copolymer can be an alternating copolymer, in which each polyoxyethylene unit derived from ethylene oxide other than the terminal unit is linked to two polyoxypropylene units and each polyoxypropylene unit derived from propylene oxide is linked to two polyoxyethylene units. The copolymer can be a block copolymer, in which at least one block or sequence of polyoxypropylene units is linked at one end or at both ends to at least one block or sequence of polyoxyethylene units. The copolymer can also be a random copolymer, in which polyoxypropylene units and polyoxyethylene units are linked in a random manner, or a copolymer containing more than one kind of sequence, for example a random sequence linked to a block of polyoxyethylene units.

In a preferred embodiment, the polyoxyethylenepolyoxypropylene copolymer can be represented by the formula

in which [C$_2$H$_4$O] represents an oxyethylene unit derived from ethylene oxide, [C$_3$H$_6$O] represents an oxypropylene unit derived from propylene oxide, a represents the total number of oxyethylene units in the copolymer, b represents the total number of oxypropylene units in the copolymer, a and b individually represent integers from 3 to 500 and the sum of a and b is at least 20.

In a particularly preferred composition according to this invention, the polyoxyethylenepolyoxypropylene copolymer can be a triblock copolymer in which a polyoxypropylene block is linked at each end to a polyoxyethylene block, or a polyoxyethylene block is linked at each end to a polyoxypropylene block. Such triblock copolymers can be represented by the formulas

and

in which each of c, d, e, and f individually represents an integer from 1 to 499, provided that the sum of c and d is equal to a and the sum of e and f is equal to b, and a and b are as defined above.

Commercially available grades of polyoxyethylenepolyoxypropylene copolymers useful in compositions of this invention include water soluble and water dispersible grades of the above triblock copolymers in liquid, paste, and flake form. For best results refined grades of polyoxyethylenepolyoxypropylene triblock copolymer in which the content of oxirane, methyloxirane, 1,4-dioxane, and methyl-substituted 1,4-dioxane impurities has been reduced to the lowest practicable levels if not to zero are preferred.

Selected and preferred polyoxyethylenepolyoxypropylene triblock copolymers represented by the formula

are commercially available under the non-proprietary name Poloxamer and described in an NF 18 (National Formulary, 18th edition) Official Monograph; see NF 18 at pages 2279–2281, which description is here incorporated by reference.

The preferred corticoid analgesic that can be used in the combination according to this invention is hydrocortisone. Other corticoid analgesics that can be used include prednisolone, dexamethasone, triamcinolone acetonide, and fluocinolone acetonide. In the topical composition of the invention the level of corticoid analgesic can range from 0.1% to 6%, preferably from 0.5% to 3%.

The preferred arylpropionic acid type analgesic that can be used in the combination according to this invention is ibuprofen. Other arylpropionic acid type analgesics that can be used include flurbiprofen, indomethacin, ketoprofen, and naproxen. In the topical composition of the invention the level of arylpropionic acid type analgesic can range from 0.5% to 15%, preferably from 2% to 8%.

The preferred p-aminobenzoic acid ester local anesthetic that can be used in the combination according to this invention is lidocaine. Other p-aminobenzoic acid ester local anesthetics that can be used include pharmaceutically acceptable salts of lidocaine such as the hydrochloride, procaine and its hydrochloride and benzocaine. In the topical composition of the invention the level of p-aminobenzoic acid ester local anesthetic can range from 0.1% to 10%, preferably from 0.5% to 5%.

The preferred capsaicin ingredient that can be used in the combination according to this invention is purified crystalline capsaicin, the cyclic amide responsible for the pungency of Capsicum peppers. Capsaicin is known to be highly irritating at concentrations of 1:1,000,000 and highly toxic when taken in large doses. Yet in the composition of this invention it is unexpectedly well tolerated and enhances the effectiveness of the combined ingredients. Other capsaicin ingredients that can be used include capsicum oleoresin and whole cayenne pepper. In the topical composition of the invention the level of capsaicin ingredient calculated as crystalline capsaicin can range from 0.005% to 0.5%, preferably from 0.02% to 0.1%.

In the topical composition of this invention, the combined remedies comprise from 5% to 25% of the volume of the composition, preferably from 8% to 12% by volume. The phospholipid comprises from 5% to 50% of the volume of the composition, preferably from 10% to 30% by volume. The polyoxyethylenepolyoxypropylene copolymer comprises from 2 to 15% of the volume of the composition, preferably from 4 to 10% by volume. The relative proportions of phospholipid and polyoxyethylenepolyoxypropylene copolymer are in the range of 25:1 to 1:3, preferably 5:1 to 1:1.

The topical composition of this invention can additionally include one or more topically acceptable carrier materials to facilitate the compounding and application of the composition. Suitable carrier materials include fatty acid alkyl esters having thirteen to thirtysix carbon atoms, ethanol, and water. Preferred fatty acid alkyl esters include methyl laurate, methyl myristate, methyl palmitate, methyl stearate, methyl behenate, ethyl oleate, ethyl linoleate, butyl oleate, butyl stearate, isopropyl myristate, isopropyl palmitate, dodecyl acetate, tetradecyl octanoate, cetyl palmitate and stearyl stearate. When present, topically acceptable carrier materials can comprise up to 60% of the volume of the composition, preferably up to 40%.

The topical composition of this invention can be presented in any convenient consistency for ease of application. A particularly preferred consistency is a cream, which can range from a pourable consistency like dairy cream to a thickened consistency like shaving cream.

The topical composition of this invention can be applied to the user's skin by the user's own hand or by the practitioner. Modest doses of the composition in the range from 0.1 to 10 ml twice daily are usually sufficient.

The topical composition of this invention can be prepared in any convenient manner. Where it is desired to avoid the effect of heat on a possibly sensitive remedy, heating to assist blending of phospholipid and/or polyoxyethylenepolyoxypropylene copolymer with a suitable carrier is best done before adding such remedy or simply avoided.

The Examples that follow are provided for purpose of illustration and not of limitation. Wherever water is shown to be used, it is "preserved water", that is water containing a known preservative to limit the growth of bacteria and other microorganisms that can consume or adversely affect the potency of a remedy. Preserved water is prepared as follows:

Methyl paraben NF 1.9 grams and propyl paraben NF 0.96 g are dissolved in 200 ml distilled water and made up with distilled water to a volume of 1 gallon. The preserved water is kept under refrigeration.

EXAMPLE 1

Preparation of a polyoxyethylenepolyoxypropylene copolymer gel.

A commercial water soluble flake grade of polyoxyethylenepolyoxypropylene triblock copolymer 80 grams and sufficient preserved water for a total volume of 400 ml were mixed in a Braun® mixer and refrigerated until the following day to hydrate.

EXAMPLE 2

Preparation of concentrated lecithin solution.

Isopropyl palmitate 200 ml was poured over 200 g soya lecithin granules without mixing and kept at room temperature until the following day to dissolve the granules and yield a viscous liquid product.

EXAMPLE 3
Preparation of a topical composition vehicle.

A 400 ml portion of concentrated lecithin solution as prepared according to Example 2 was placed in a mixer and mixed at slow speed for 5 minutes. A 400 ml portion of cold (refrigerated) copolymer gel as prepared according to Example 1 was added quickly and mixed at high speed until a thick readily spreadable cream was obtained and discharged into a storage jar.

EXAMPLE 4
Preparation of topical compositions for relieving pain.

The procedure of Example 3 was followed except that the desired combination of remedies was added to a 186 ml portion of the concentrated lecithin solution in the mixer and mixed at slow speed for 5 minutes before adding 185 ml of the cold copolymer gel. The remedies and quantities used are tabulated below.

| EXAMPLE INGREDIENT | 4 AMOUNT |
|---|---|
| CAPSAICIN* | 0.3 ML |
| IBUPROFEN | 18 GRAMS |
| LIDOCAINE | 7.2 GRAMS |
| BENZOCAINE | 7.2 GRAMS |
| HYDROCORTISONE | 7.2 GRAMS |

*SOLUTION MADE WITH 25 GRAMS CRYSTALLINE CAPSAICIN AND PHARMACEUTICAL GRADE ALCOHOL AND DILUTED TO 100 ML

What is claimed is:

1. A topical composition for relieving pain in a person in need of such relief, consisting essentially of an effective amount of a combination of hydrocortisone, ibuprofen, and at least one of lidocaine and benzocaine; an amount of capsaicin effective in enhancing the effectiveness in relieving pain of said combination, and an amount effective to increase the transmission of said combination through the skin of at least one phospholipid and at least one polyoxyethylenepolyoxypropylene copolymer.

2. A topical composition according to claim 1 in which the phospholipid is lecithin.

3. A topical composition according to claim 1 in which the concentration of phospholipid is in the range of 5 to 50 milliliters per 100 milliliters of composition.

4. A topical composition according to claim 1 in which the concentration of polyoxyethylenepolyoxypropylene copolymer is in the range of 2 to 15 milliliters per 100 milliliters of composition.

5. A topical composition according to claim 1 in which the relative proportions of phospholipid and polyoxyethylenepolyoxypropylene copolymer are in the range of 25:1 to 1:3.

6. A topical composition according to claim 1 with at least one topically acceptable carrier added, selected from the group consisting of fatty acid alkyl esters having thirteen to thirty-six carbon atoms, ethanol, and water.

7. A topical composition according to claim 1 which is a cream.

8. The method of relieving pain of a person in need of such relief, comprising topically administering to said person a topical composition according to claim 1 for a period of time sufficient to achieve relief of pain.

9. The method of claim 8 in which the quantity of composition administered daily is in the range of 0.1 to 10 milliliters.

10. A topical composition according to claim 1 in which the local anesthetic is lidocaine.

11. A topical composition according to claim 1 in which the local anesthetic is benzocaine.

12. A topical composition according to claim 1 in which the level of hydrocortisone is in the range from 0.5% to 3% by weight of the composition.

13. A topical composition according to claim 1 in which the level of ibuprofen is in the range from 2% to 8% by weight of the composition.

14. A topical composition according to claim 1 in which the level of lidocaine is in the range from 0.5% to 5% by weight of the composition.

15. A topical composition according to claim 1 in which the level of capsaicin is in the range from 0.02% to 0.1% by weight of the composition.

16. A topical composition according to claim 1 in which the level of hydrocortisone is in the range from 0.5% to 3% by weight of the composition, the level of ibuprofene is in the range from 2% to 8% by weight of the composition, the level of lidocaine is in the range from 0.5% to 5% by weight of the composition, and the level of capsaicin is in the range from 0.02% to 0.1% by weight of the composition.

17. The method of claim 8 in which a topical composition is topically applied to a person in need of relief of pain in a part of the body distant from the area to which the composition is applied.

* * * * *